United States Patent [19]

Nimry et al.

[11] Patent Number: 4,673,767

[45] Date of Patent: Jun. 16, 1987

[54] AMS-1B CRYSTALLINE BOROSILICATE MOLECULAR SIEVE-BASED CATALYST COMPOSITIONS AND PROCESS FOR TOLUENE ALKYLATION

[75] Inventors: Tayseer S. Nimry, Glen Ellyn; Richard E. De Simone, Lisle, both of Ill.

[73] Assignee: Amoco Corporation, Chicago, Ill.

[21] Appl. No.: 801,471

[22] Filed: Nov. 25, 1985

[51] Int. Cl.[4] .............................................. C07C 2/68
[52] U.S. Cl. .................................................... 585/467
[58] Field of Search ........................................ 585/467

[56] References Cited

U.S. PATENT DOCUMENTS 4,491,678  1/1985  Oda et al. ............................ 585/467

Primary Examiner—Curtis R. Davis

Attorney, Agent, or Firm—Reed F. Riley; William H. Magidson; Ralph C. Medhurst

[57] ABSTRACT

Described are catalyst compositions comprising a HAMS-1B crystalline borosilicate molecular sieve incorporated into an inorganic matrix, which have been impregnated with a magnesium compound or with both a phosphorus compound and a magnesium compound, said impregnated compositions having improved para-selectively for toluene alkylation. Such impregnated compositions, when used for the alkylation of toluene using methanol, methylether, ethylene, or propylene yield dialkylbenzene products containing a higher proportion of the para-isomer than corresponding unimpregnated borosilicate-based compositions. When toluene is alkylated with propylene using the impregnated catalyst compositions of this invention, a significant increase in para-selectivity among the cymene isomers is obtained at high total-cymene/n-propyltoluene ratios.

12 Claims, No Drawings

4,673,767

AMS-1B CRYSTALLINE BOROSILICATE MOLECULAR SIEVE-BASED CATALYST COMPOSITIONS AND PROCESS FOR TOLUENE ALKYLATION

BACKGROUND OF THE INVENTION

This invention relates to improved AMS-1B crystalline molecular sieve-based catalyst compositions, and particularly, to the use of such compositions having improved para selectivity for aromatics alkylation. More particularly, it relates to processes for using these improved compositions to selectively para-propylate toluene to paracymene.

In U.S. Pat. No. 4,532,226, a ZSM-5 aluminosilicate zeolite catalyst modified by P and Cr, Mo, or W and used to selectively catalyze formation of the 1,4-dialkyl isomer during conversion of aromatic compounds is described. U.S. Pat. No. 4,518,703 teaches a P modified silica polymorph-based catalyst for the methylation of toluene. In U.S. Pat. Nos. 4,504,690, 4,128,592 and 4,086,287 is taught modifying a ZSM-5 aluminosilicate zeolite catalyst with P, Mg or P/Mg oxides to obtain high proportions of the 1,4-dialkyl isomer. Phosphorus modification of a ZSM-5 zeolite catalyst for the alkylation of toluene to form a higher proportion of p-xylene is shown in J. Appl. Polymer Sci. 36, 209 (1981) as are P or Mg modified ZSM-5 zeolite catalysts for the disproportionation of toluene. Selective para-alkylation using P modified ZSM-5 zeolite catalysts is again described in J. Cat. 67, 159 (1981). Conversion of olefins over the same type of catalyst is shown in J. Cat. 61, 155 (1980). Disproportionation of toluene to produce benzene over P, Mg modified crystalline aluminosilicate zeolite catalysts is described in U.S. Pat. No. 4,137,195. Alkylation or disproportionation of certain monosubstituted benzene compounds to achieve nearly 100% selectivity to paradisubstituted derivates over phosphorous and magnesium compound-modified ZSM-5 type zeolite catalysts is reported in J. Am. Chem. Soc. 101, 6783 (1979).

Propylation of toluene with the selective production of cymenes (higher iso/normal ratio) over an unmodified ZSM-5 aluminosilicate of zeolite catalyst is described in U.S. Pat. No. 4,049,737.

Use of Mg alone or in combination with P to modify a ZSM-5 aluminosilicate of zeolite catalyst is described in U.S. Pat. No. 4,049,573 and the modified catalyst is used for converting alcohols and ethers to hydrocarbons. Again, Mg is used to modify ZSM-5 zeolite catalysts in U.S. Pat. No. 4,002,698 which can be used for selective production of p-xylene from charge stocks of toluene and a $C_3$-$C_{10}$ olefin; P modified catalysts for the methylation of toluene are also described. Phosphorus modified ZSM-5 aluminosilicate zeolite catalysts are again described in U.S. Pat. No. 3,972,832 and described as useful for the conversion of aliphatics to various products.

Catalyst compositions, generally useful for hydrocarbon conversion, based upon AMS-1B crystalline borosilicate molecular sieve have been described in U.S. Pat. Nos. 4,268,420; 4,269,813; 4,285,919 and Published European Application No. 68,796.

As described in the references in the paragraph above, catalyst compositions typically are formed by incorporating an AMS-1B crystalline borosilicate molecular sieve material into a matrix such as alumina, silica or silica-alumina to produce a catalyst formulation. In one method of making AMS-1B crystalline borosilicate, sieve is formed by crystallizing sources for silicon oxide and boron oxide with sodium hydroxide and an organic compound. After crystallization, the resulting sodium form is ion exchanged with an ammonium compound and calcined to yield the hydrogen form of AMS-1B. In another and more preferred method, AMS-1B crystalline borosilicate is crystallized in the hydrogen form from a mixture containing a diamine in place of a metal hydroxide. This method tends to reduce the amount of alkali metal ion, e.g. Na+, in the final catalyst composition. AMS-1B borosilicates in hydrogen form are designated HAMS-1B. Typically, the hydrogen form sieve is gelled with an alumina sol, dried and calcined to yield a catalyst composition.

SUMMARY OF THE INVENTION

Described herein are improved catalyst compositions comprising a HAMS-1B crystalline borosilicate molecular sieve incorporated into a matrix, which have been impregnated with a small amount of a suitable magnesium compound or a small amount of both a suitable phosphorus compound and a suitable magnesium compound, said impregnated compositions showing improved para-selectivity for toluene alkylation. Also described are processes for the alkylation of toluene carried out by contacting such impregnated catalyst compositions and methyl alcohol, dimethyl ether, ethylene or propylene under conversion conditions, which yield dialkylbenzene products containing a higher proportion of the para isomer as compared with unimpregnated borosilicate-based compositions. In particular, when toluene is alkylated with propylene using these impregnated catalyst compositions, a significant increase in para selectivity among the cymene isomers is obtained at high cymene/n-propyltoluene ratios.

DETAILED DESCRIPTION OF THE INVENTION

The catalyst compositions used in this invention are based on AMS-1B crystalline borosilicate molecular sieve, which is described in U.S. Pat. Nos. 4,268,420; 4,269,813; and 4,285,919 and Published European Patent Application No. 68,796, all incorporated herein by reference. AMS-1B crystalline borosilicate generally can be characterized by the X-ray pattern listed in Table A and by the composition formula:

$$0.9 \pm 0.2 M_{2/n}O:B_2O_3:ySiO_2:zH_2O$$

wherein M is at least one cation, n is the oxidation state of the cation, y is between 4 and about 600 and z is between 0 and about 160.

TABLE A

| d-Spacing Å (1) | Assigned Strength (2) |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

(1) Copper K alpha radiation
(2) VW = very weak; W = weak; M = medium; MS = medium strong; VS = very strong The AMS-1B borosilicate molecular sieve useful in this invention can be prepared by crystallizing an aqueous mixture, at a controlled pH, of sources for cations, an oxide of boron, an oxide of silicon, and an organic template compound.

Typically, the mol ratios of the various reactants can be varied to produce the crystalline borosilicates of this invention. Specifically, the mol ratios of the initial reactant concentrations are indicated below:

|  | Broad | Preferred | Most Preferred |
|---|---|---|---|
| $SiO_2/B_2O_3$ | 5–400 | 10–150 | 10–80 |
| $R_2O^+/[R_2O^+ + M_{2/n}O]$ | 0.1–1.0 | 0.2–0.97 | 0.3–0.97 |
| $OH^-/SiO_2$ | 0.01–11 | 0.1–2 | 0.1–1 |
| $H_2O/OH^-$ | 10–4000 | 10–500 | 10–500 | wherein R is an organic compound and M is at least one cation having the oxidation state n, such as an alkali or an alkaline earth metal cation or hydrogen. By regulation of the quantity of boron (represented as $B_2O_3$) in the reaction mixture, it is possible to vary the $SiO/B_2O_3$ molar ratio in the final product.

More specifically, the material useful in the present invention is prepared by mixing a base, a boron oxide source, and an organic template compound in water (preferably distilled or deionized). The order of addition usually is not critical although a typical procedure is to dissolve base and boric acid in water and then add the template compound. Generally, the silicon oxide compound is added with intensive mixing such as that performed in a Waring Blendor and the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of materials affording silicon oxide useful in this invention include silicic acid, sodium silicate, tetraalkyl silicates and Ludox, a stabilized polymer of silicic acid manufactured by E. I. DuPont de Nemours & Co. Typically, the oxide of boron source is boric acid although equivalent species can be used such as sodium borate and other boron-containing compounds.

Cations useful in formation of AMS-1B crystalline borosilicate include alkali metal and alkaline earth metal cations such as sodium, potassium, lithium, calcium and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly and more preferably by the hydrogen form by replacing such metal cation hydroxides with an organic base such as ethylenediamine as described in Published European Application No. 68,796.

Organic templates useful in preparing AMS-1B crystalline borosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about $11.0\pm0.2$ using a compatible acid or base such as sodium bisulfate or sodium hydroxide. After sufficient quantities of a silica source such as a silicic acid polymer (Ludox) are added with intensive mixing, preferably the pH is again checked and adjusted to a range of about $11.0\pm0.2$.

Alternatively and more preferably, AMS-1B crystalline borosilicate molecular sieve can be prepared by crystallizing a mixture of sources for an oxide of silicon, an oxide of boron, an alkyl ammonium compound and ethylenediamine such that the initial reactant molar ratios of water to silica range from about 5 to about 25, preferably about 5 to about 20 and most preferably from about 10 to about 15. In addition, preferable molar ratios for initial reactant silica to oxide of boron range from about 4 to about 150, more preferably from about 5 to about 80 and most preferably from about 5 to about 20. The molar ratio of ethylenediamine to silicon oxide should be above about 0.05, typically below 5, preferably between about 0.1 and about 1.0 and most preferably between about 0.2 and 0.5. The molar ratio of alkylammonium compound, such as tetra-n-propylammonium bromide, to silicon oxide can range from 0 to about 1 or above, typically above about 0.005, preferably about 0.01 to about 0.1, more preferably about 0.01 to about 0.1 and most preferably about 0.02 to about 0.05.

The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about one to about seven days, at a temperature ranging from about 100° C. to about 250° C., preferably about 125° C. to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50°–225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° C. to about 850° C. and preferably from about 425° C. to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

A catalytically active material can be placed onto the borosilicate structure, either before or after incorporation into a matrix, by ion exchange, impregnation, a combination thereof, or other suitable contact means. Before placing a catalytically active metal ion or compound on the borosilicate structure, the borosilicate should be in the hydrogen form, i.e., HAMS-1B If the sieve was prepared using a metal hydroxide, such as sodium hydroxide, the hydrogen form typically, is produced by exchange one or more times with ammonium ion, typically using ammonium acetate, followed by drying and calcination as described above.

The original cation in the AMS-1B crystalline borosilicate can be replaced all or in part by ion exchange with other cations including other metal ions and their amine complexes, alkylammonium ions, ammonium ions, hydrogen ions, and mixtures thereof. Preferred replacing cations are those which render the crystalline borosilicate catalytically active, especially for hydrocarbon conversion. Typical catalytically active ions include hydrogen, metal ions of Groups IB, IIA, IIB, IIIA, VB, VIB and VIII, and of manganese, vanadium, chromium, uranium, and rare earth elements.

Also, water soluble salts of catalytically active materials can be impregnated onto the crystalline borosilicate of this invention. Such catalytically active materials include metals of Groups IB, IIA, IIB, IIIA, IIIB, IVB, VB, VIB, VIIB, and VIII, and rare earth elements.

Examples of catalytically active elements include ruthenium, rhodium, iron, cobalt, and nickel. Mixtures of elements can be used. Other catalytic materials include ions and compounds of aluminum, lanthanum, molybdenum, tungsten, and noble metals such as ruthenium, osmium, rhodium, iridium, palladium, and platinum. Other additional catalytic materials can be ions and compounds of scandium, yttrium, titanium, zirconium, hafnium, vanadium, niobium, tantalum, chromium, cerium, manganese, cobalt, iron, zinc and cadmium. Specific combinations of non-noble metals of Group VIII and other catalytic materials include ions or compounds of nickel and osmium, nickel and lanthanum, nickel and palladium, nickel and iridium, nickel and molybdenum, and nickel and tungsten.

Ion exchange and impregnation techniques are well-known in the art. Typically, an aqueous solution of a cationic species is exchanged one or more times at about 25° C. to about 100° C. A hydrocarbon-soluble metal compound such as a metal carbonyl also can be used to place a catalytically active material. Impregnation of a catalytically active compound on the borosilicate or on a composition comprising the crystalline borosilicate suspended in and distributed throughout a matrix of a support material, such as a porous refractory inorganic oxide such as alumina, often results in a suitable catalytic composition. A combination of ion exchange and impregnation can be used. Presence of sodium ion in a composition usually is detrimental to catalytic activity.

The amount of catalytically active material placed on the AMS-1B borosilicate can vary from about 0.01 weight percent to about 30 weight percent, typically from about 0.05 to about 25 weight percent, depending on the process use intended. The optimum amount can be determined easily by routine experimentation.

The AMS-1B crystalline borosilicate useful in this invention is admixed with or incorporated within various binders or matrix materials depending upon the intended process use. The crystalline borosilicate can be combined with active or inactive materials, synthetic or naturally-occurring zeolites, as well as inorganic or organic materials which would be useful for binding the borosilicate. Well-known materials include silica, silica-alumina, alumina, magnesia, titania, zirconia, alumina sols, hydrated aluminas, clays such as bentonite or kaolin, or other binders well-known in the art. Typically, the borosilicate is incorporated within a matrix material by blending with a sol of the matrix material and gelling the resulting mixture. Also, solid particles of the borosilicate and matrix material can be physically admixed. Typically, such borosilicate compositions can be pelletized or extruded into useful shapes. The crystalline borosilicate content can vary anywhere from a few up to 100 wt. % of the total composition. Catalytic compositions can contain about 0.1 wt. % to about 100 wt. % crystalline borosilicate material and preferably contain about 10 wt. % to about 95 wt. % of such material and most preferably contain about 20 wt. % to about 80 wt. % of such material.

Catalyst compositions impregnated with a magnesium compound and a phosphorus compound or a magnesium compound according to this invention can be in powder form or already in extrudate or pellet form.

To make the impregnated catalyst compositions of this invention, a composition comprising the acid form of the crystalline borosilicate, HAMS-1B, molecular sieve in an inorganic matrix is contacted with a phosphorus compound-containing solution. The resulting mass is then dried at temperatures up to about 150° C. removing in this step essentially all of the impregnation solvent. The resultant composition is then activated by calcination for 3 hours to about 24 hours at about 350° C. to about 650° C., more preferably about 4 hours to about 24 hours at about 400° C. to about 600° C. Care should be taken to avoid catalyst degration during calcination.

The amount of phosphorus incorporated with the catalyst composition should be from about 0.5 to about 25 percent by weight, especially from about 1 to about 15 percent by weight, percents calculated as percent of the element.

Representative phosphorus compounds useful in the impregnation step include derivatives of groups represented by the formulae $PX_3$, $RPX_2$, $R_2PX$, $R_3P$, $X_3PO$, $(XO_3)PO$, $(XO)_3P$, $R_3P=O$, $R_3P=S$, $RPO_2$, $PPS_2$, $RP(O)(OX)_2$, $RP(S)(SX)_3$, $R_2P(O)OX$, $R_2P(S)SX$, $RP(OX)_2$, $RP(SX)_2$, $ROP(OX)_2O$, $RSP(SX)_2$, $(RS)_2PSP(SR)_2$ and $(RO)_2POP(OR)_2$ wherein R is alkyl or aryl and X is hydrogen, alkyl, aryl or halide. These compounds include primary, secondary or tertiary phosphines; tertiary phosphine oxides; tertiary phosphine sulfides; primary and secondary phosphonic acids and their corresponding sulfur derivatives; esters of phosphonic acids; the dialkyl alkyl phosphonates; alkyl dialkyl phosphonates; phosphinous acids, primary, second and tertiary phosphites and esters thereof; alkyl dialkylphosphinites, dialkyl alkylphosphonites their esters and sulfur derivatives.

Other suitable phosphorus-containing compounds include the phosphorus halides such as phosphorus trichloride, phosphorus tribromide, phosphorus triiodide, alkyl phosphorodichlorides, dialkyl phosphorochlorides and dialkyl phosphonochloridites. Preferred phosphorus-containing compounds include phosphoric acid, phosphite esters such as triethylphosphite, ammonium hydrogen phosphate and ammonium dihydrogen phosphate.

Magnesium compounds can be incorporated with the catalyst compositions in a manner similar to that employed with the phosphorus compounds above. Magnesium impregnation should result in about 4% to 25% by weight magnesium, preferably from about 8% to about 15% by weight magnesium, percents calculated as the element. As with phosphorus, magnesium compound incorporation is effected by contacting the catalyst composition with the solution of an appropriate magnesium compound followed by drying and calcining to substantially convert impregnated magnesium compound to its oxide form. Preferred magnesium-containing compounds include most soluble magnesium salts, more preferably magnesium nitrate or acetate. Drying and calcination times and temperatures are generally the same as recited hereinbefore for drying and calcination of phosphorus-containing catalyst compositions.

The solutions of phosphorus or magnesium compounds used in impregnation may be made from polar or non-polar solvents, including water and organic solvents generally. Solvents that are destructive of either the zeolite or matrix should be avoided. Water and alcohols are preferred solvents.

Generally, the phosphorus compound and the magnesium compound are impregnated in the catalyst composition sequentially with phosphorus impregnation preceding magnesium impregnation.

Methylation of toluene in the presence of the above-described catalyst compositions is effected by contact of the toluene with a methylating agent, preferably methanol or dimethyl ether, at a temperature between about 250° C. and about 700° C. and preferably between about 400° C. and about 600° C. The reaction generally takes place at atmospheric pressure, but the pressure may be within the approximate range of about 1 atmosphere to about 2000 psig. The molar ratio of methylating agent to toluene is generally between about 0.05 and about 5, preferably about 0.1 to about 1. When methanol is employed as the methylating agent a suitable molar ratio of methanol to toluene has been found to be approximately about 0.1-2 moles of methanol per mol of toluene. With the use of other methylating agents, such as acetaldehyde, dimethoxyethane, acetone, and methyl halides, the molar ratio of methylating agent to toluene may vary within the aforenoted range.

Reaction is suitably accomplished utilizing a weight hourly space velocity of between about 0.2 and about 500 and preferably between about 1 and about 100. The reaction product consisting predominantly of para-xylene or a mixture of para- and meta-xylene together with comparatively smaller amounts of ortho-xylene may be separated by any suitable means, such as by passing the same through a fractional crystallization process coupled with distillation.

In effecting the catalyzed alkylation of toluene with ethylene, conversion conditions include a temperature between about 250° C. and about 600° C., pressure between about 1 atmosphere and about 2000 psig, utilizing a feed weight hourly space velocity between about 0.1 and about 100, and a molar feed ratio of toluene/ethylene between about 0.5 and about 50, preferably between about 1 and about 10.

Propylation of toluene in the presence of the above-described catalyst compositions is effected by contact of the toluene with propylene at a temperature between about 200° C. and about 600° C. and preferably between about 250° C. and about 400° C. The reaction generally takes place at atmospheric pressure, but the pressure may be within the approximate range of about 1 atmosphere to about 2000 psig. The molar ratio of toluene to propylene employed is within the approximate range of about 0.5 to about 50. Reaction is suitably accomplished utilizing a weight hourly space velocity of between about 0.1 and about 100 and preferably between about 0.5 and about 50. The reaction product consisting selectively of paracymene with comparatively smaller amounts of n-propyltoluenes may be separated by any suitable means.

The following Examples will serve to illustrate certain specific embodiments of the hereindisclosed invention. These Examples should not, however, be construed as limiting the scope of the novel invention as there are many variations which may be made thereon without departing from the spirit of the disclosed invention, as those of skill in the art will recognize.

EXAMPLES

General

The reactions in the hydrocarbon conversion Examples below were carried out in a stainless steel reactor of plug-flow design. Reactants were mixed and then fed into a preheater packed with inert Denstone packing and passed into a ½-inch O.D.×5-inch reactor tube filled with a 3-5 g catalyst composition charge. The entire reactor and preheater assembly is supported in a fluidized sand bath maintained at reaction temperature. Product is collected in a cooled vessel as it drips from the reactor and analyzed by gas chromatography on a 60 meter fused silica capillary column. All hydrocarbon isomer amounts are given in percents by weight. Phosphorus and magnesium amounts are given in weight percent of the element.

COMPARATIVE EXAMPLE 1

This catalyst composition was made from 40% by weight HAMS-1B sieve and 60% by weight alumina. Thus, 118 g of HAMS-1B was gelled with 1810 g of American Cyanamide PHF alumina sol, 9.47% by weight alumina content, using 171 ml of concentrated ammonium hydroxide (29% $NH_3$) and 236 g of water. The gel was dried at 165° C. for 18 hours. The dried sample was ground to 18-40 mesh then calcined at 538° C. for 12 hours.

EXAMPLE 2

In a small beaker containing 38 g of water was dissolved 9.29 g of $NH_4H_2PO_4$. The solution was then added slowly to 25 g of the catalyst composition of Example 1 while stirring with a glass rod. The sample was dried at 130° C. for 16 hours and then calcined at 538° C. for 12 hours. This impregnated catalyst composition contained approximately 7.8% phosphorus by weight.

EXAMPLE 3

An impregnated catalyst composition was prepared as in Example 2 by using 18.57 g of $NH_4H_2PO_4$ and 25 g of the catalyst composition of Example 1. The modified catalyst composition contained approximately 15% phosphorus by weight.

EXAMPLE 4

Six grams of the impregnated catalyst composition of Example 2 was placed in a solution of 8.37 g of $Mg(NO_3)_2.6H_2O$ dissolved in 15 ml of water. The suspension was allowed to stand overnight at room temperature, then dried on a rotary evaporator. After drying further in a 150° C. oven for 1 hour, the temperature of the oven was slowly increased at ½ hour intervals until 500° C. was reached, and held at this temperature overnight. Upon cooling the magnesium/phosphorus impregnated catalyst composition was ready for use. It contains about 10.6% by weight magnesium in addition to its phosphorus content.

EXAMPLE 5

The catalyst composition of Example 3 was treated with $Mg(NO_3)_2.6H_2O$ as in Example 4. It contains about 10.6% by weight magnesium in addition to its phosphorus content.

COMPARATIVE EXAMPLE 6

Four grams of the catalyst composition of Example 1 was placed in the reactor and heated to 400° C. under a stream of argon. A solution of toluene and methanol in mole ratio of 4:1 (toluene:methanol) was fed at a rate of 0.21 ml/min. Analysis of the product showed xylenes to be the dominant product with isomeric percentages of:
o-xylene: 22.9%
m-xylene: 53.0%
p-xylene: 24.1%.

COMPARATIVE EXAMPLE 7

Three grams of the catalyst composition of Example 1 was placed in the reactor and heated to 300° C. under a stream of argon. Toluene was then fed at 0.21 ml/min. and ethylene at 5.5 ml/min.; this is a toluene:ethylene mol ratio of approximately 8:1. Analysis of the product shows ethyltoluenes to be the dominant product with isomeric percentages of:
o-ethyltoluene: 12.8%
m-ethyltoluene: 58.4%
p-ethyltoluene: 28.8%.

EXAMPLE 8

Six grams of the impregnated catalyst composition of Example 4 was placed in the reactor and reacted as in Example 6. Analysis showed:
o-xylene: 18.0%
m-xylene: 37.5%
p-xylene: 44.5%.

EXAMPLE 9

A 6.9 g portion of the catalyst composition of Example 5 was placed in the reactor and reacted as in Example 7 at 325° C. The results showed ethyltoluenes as the only significant product. The isomeric ratios of the product were:
o-ethyltoluene: <0.05%
m-ethyltoluene: 6.9%
p-ethyltoluene: 93.1%.

EXAMPLE 10

A 6.7 g portion of the catalyst composition of Example 4 was placed in the reactor and reacted at 300° C. as in Example 20. The product analyzed as:
o-isopropyltoluene: 0.05%
m-isopropyltoluene: 2.8%
p-isopropyltoluene: 97.2%.

COMPARATIVE EXAMPLE 11

A 3.0 g portion of the catalyst composition of Example 1 was placed in the reactor and heated to 300° C. under a stream of argon. Toluene was then fed at 0.21 ml/min. and ethylene was fed at 5.5 ml/min. (approximately an 8:1 mol ratio toluene:ethylene) for a period of 90 minutes. Analysis of the product showed:
7.0%: o-ethyltoluene
63.4%: m-ethyltoluene
29.6%: p-ethyltoluene
The equilibrium concentration of ethyltoluene isomers is 18.3% ortho, 50.2% meta and 31.5% para.

EXAMPLE 12

A 6.0 g portion of the catalyst composition of Example 1 in 1/16" extrudate form was placed in a solution of 8.27 g $Mg(NO_3)_2.6H_2O$ dissolved in 15 ml of water. The suspension was heated in a water bath at 92° C. for one hour, cooled and stirred for an additional two hours, and then left undisturbed overnight. After 1½ hours in a drying oven at 110° C. to remove bulk water, the material was placed in a calcining oven. The temperature of the oven was slowly increased at ½ hour intervals until 500° C. was reached, and held at this temperature overnight. Upon cooling the catalyst composition is ready for use. This catalyst composition contains about 10.6% by weight magnesium.

EXAMPLE 13

A 4.6 g portion of the catalyst composition of Example 12 was placed in the reactor. The conditions and procedure were the same as in Example 11. Analysis of the product showed:
<0.5%: o-ethyltoluene
35.2%: m-ethyltoluene
64.8%: p-ethyltoluene.

EXAMPLE 14

A 10 g sample of the catalyst composition of Example 1 in 1/16" extrudate form was placed in a solution of 16 g of 85% phosphoric acid in 20 ml of water and allowed to soak overnight. The extrudate was filtered, dried and calcined as in Example 12. These phosphorus impregnated extrudates were then treated further by soaking overnight in a solution of 25 g of $Mg(OAc)_2.4H_2O$ in 20 ml of water. This catalyst was filtered, dried at 120° C. for 2 hours, then calcined at 500° C. The catalyst composition contains approximately 13% by weight phosphorus and approximately 10% by weight magnesium.

EXAMPLE 15

A 8.0 g sample of the catalyst composition of Example 14 was placed in the reactor and ethylation carried out as in Example 12. Analysis of the product showed:
<0.05%: o-ethyltoluene
21.1%: m-ethyltoluene
78.9%: p-ethyltoluene.

EXAMPLE 16

A 7.0 g sample of the catalyst composition of Example 1 was impregnated with about 20% by weight phosphorus using $NH_4H_2PO_4$, a sample placed in the reactor and the reaction carried out as in Example 12. Analysis of the product showed:
8.0%: o-ethyltoluene
41.6%: m-ethyltoluene
50.4%: p-ethyltoluene.

EXAMPLE 17

A 6.0 g portion of catalyst composition of Example 16 was placed in a solution of 8.37 g $Mg(NO_3)_2.6H_2O$ in 15 ml of water. The suspension was allowed to stand overnight at room temperature. The suspension was dried on a rotary evaporator and then calcined as in previous Examples. This catalyst composition contained about 20% by weight phosphorus and about 10.6% by weight magnesium.

EXAMPLE 18

A 7.1 g portion of the catalyst composition of Example 17 was placed in the reactor and the ethylation reaction carried out as in Example 12. Analysis of the product showed:
<0.05%: o-ethyltoluene
11.2%: m-ethyltoluene
88.8%: p-ethyltoluene.

EXAMPLE 19

The catalyst composition of Example 17 was ethylated for 16 hours, then calcined to remove coke deposit. It was then reloaded into the reactor and the reaction was continued for an additional 13 hours, during which time (after 6 hours) the reaction temperature was lowered to 325° C. and the toluene to ethylene ratios were varied from 8:1 to 4:1 to 2:1. The results of these experiments are tabulated below:

TABLE

| Ratio Toluene/Ethylene | % o-Et | % m-Et | % p-Et |
| --- | --- | --- | --- |
| 8:1 | <0.05 | 7.0 | 93.0 |
| 4:1 | <0.05 | 6.9 | 93.1 |
| 2:1 | <0.05 | 6.8 | 93.2 |

COMPARATIVE EXAMPLE 20

A 3.0 g portion of the catalyst composition of Example 1 was placed in the reactor and heated to 250° C. under a stream of argon. Upon reaching 250° C., toluene was fed at 0.21 ml/min. and propylene was fed at 5.5 ml/min. (approximately an 8:1 mol ratio toluene:propylene) for a period of 2½ hours. Analysis of the product showed:
69.1%: p-cymene
28.3%: m-cymene
2.6%: o-cymene
Approximately 10% n-propyl and 90% isopropyl toluenes were produced in this propylation.

EXAMPLE 21

A 6.0 g portion of the catalyst composition of Example 1 sized 16–40 mesh was placed in a solution of 7.0 g of $Mg(OAc)_2.4H_2O$ in 15 ml of water and heated to about 90° C. in a water bath. This "suspension" was evaporated to dryness in a rotary evaporator, then placed in a 150° C. oven for one hour. The temperature of the oven was slowly increased at ½ hour intervals until 500° C. was reached, and held at this temperature overnight and cooled. This material contains about 11.7% by weight magnesium.

EXAMPLE 22

Four grams of the above Mg-impregnated catalyst composition was placed in the reactor. The conditions and procedure were as in Example 20. Analysis of the product showed:
76.19%: p-cymene
16.71%: m-cymene
7.63%: o-cymene.
The temperature was raised to 300° C. whereupon the product contained 89.45% p-cymene, 9.08 m-cymene and 1.50% o-cymene.

EXAMPLE 23

The procedure of Example 20 was repeated except that 8.37 g of $Mg(NO_3)_2.6H_2O$ was used instead of the $Mg(OAc)_2.4H2O$. A 4.8 g amount of this Mg-impregnated (about 10.6% by weight) catalyst composition was placed in the reactor. The conditions and procedures were the same as in Example 21 except the reaction temperature was 300° C. Analysis of the product showed:
92.86%: p-cymene
7.14%: m-cymene
<0.5%: o-cymene.

EXAMPLE 24

A 6 g portion of the catalyst composition of Example 1 impregnated with about 10% by weight phosphorus using $NH_4H_2PO_4$ was placed in a solution made from 8.37 g $Mg(NO_3)_2.6H_2O$ and dissolved in 15 ml of water. The suspension was allowed to stand overnight at room temperature, then dried on a rotary evaporator. The catalyst composition was then calcined as described in Example 21 and contained about 10.6 weight percent magnesium.

EXAMPLE 25

A 6.9 g portion of the P/Mg impregnated catalyst composition of Example 24 was placed in the reactor and the propylation carried out at 250° C. as in Example 20. The product analyzed as:
92.29%: p-cymene
4.71%: m-cymene
<0.5%: o-cymene.

What is claimed is:
1. A process for making ethyltoluene by reacting ethylene with toluene in the presence of a catalyst composition comprising a HAMS-1B crystalline borosilicate molecular sieve incorporated into an inorganic matrix, said composition (1) impregnated by a magnesium compound and subsequently heated to substantially convert said compound to the oxide form and (2) containing between about 4 and about 25% by weight magnesium.

2. A process for making ethyltoluene by reacting ethylene with toluene in the presence of a catalyst composition comprising a HAMS-1B crystalline borosilicate molecular sieve incorporated into an inorganic matrix, said composition (1) impregnated by a phosphorus compound and a magnesium compound and subsequently heated to substantially convert said compounds to the oxide forms and (2) containing between about 0.5 and about 25% by weight phosphorus and about 4 and about 25% by weight magnesium.

3. The process of claim 1 wherein said HAMS-1B molecular sieve comprises from about 20 to about 80 wt. % incorporated into an alumina, silica, or silica-alumina matrix.

4. The process of claim 2 wherein said HAMS-1B molecular sieve comprises from about 20 to about 80 wt. % incorporated into an alumina, silica, or silica-alumina matrix.

5. A process for making isopropyltoluenes by reacting propylene with toluene in the presence of a catalyst composition comprising a HAMS-1B crystalline borosilicate molecular sieve incoporated into an inorganic matrix, said composition (1) impregnated by a magnesium compound and subsequently heated to substantially convert said compound to the oxide form and (2) containing between about 4 and about 25% by weight magnesium.

6. A process for making isopropyltoluenes by reacting propylene with toluene in the presence of a catalyst composition comprising a HAMS-1B crystalline borosilicate molecular sieve incorporated into an inorganic matrix, said composition (1) impregnated by a phosphorus compound and a magnesium compound and subsequently heated to substantially convert said compounds to the oxide forms and (2) containing between about 0.5 and about 25% by weight phosphorus and about 4 and about 25% by weight magnesium.

7. The process of claim 5 wherein said HAMS-1B molecular sieve comprises from about 20 to about 80 wt. % incorporated into an alumina, silica, or silica-alumina matrix.

8. The process of claim 6 wherein said HAMS-1B molecular sieve comprises from about 20 to about 80 wt. % incorporated into an alumina, silica, or silica-alumina matrix.

9. The process of claim 5 wherein para-cymene is made selectively.

10. The process of claim 6 wherein para-cymene is made selectively.

11. The process of claim 7 wherein para-cymene is made selectively.

12. The process of claim 8 wherein para-cymene is made selectively.

* * * * *